US00PP30056P3

(12) United States Plant Patent
Olesen

(10) Patent No.: US PP30,056 P3
(45) Date of Patent: Jan. 8, 2019

(54) MINIATURE ROSE PLANT NAMED 'POULTY024'

(50) Latin Name: ***Rosa* hybrid**
Varietal Denomination: Poulty024

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/330,284

(22) Filed: Sep. 6, 2016

(65) Prior Publication Data

US 2018/0310447 P1 Oct. 25, 2018

(51) Int. Cl.
*A01H 5/02* (2018.01)
*A01H 6/74* (2018.01)

(52) U.S. Cl.
USPC ..... Plt./120
CPC ..... *A01H 5/02* (2013.01); *A01H 6/749* (2018.05)

(58) Field of Classification Search
USPC ..... Plt./120, 121, 119
CPC ..... A01H 5/0222
See application file for complete search history.

(56) References Cited

PUBLICATIONS http://floradania.dk/en/nyheder/new-varieties/new-variety/browse/29/art/emitm-partyr-poulty024n/; Mar. 12, 2015; 2 pages.*

* cited by examiner

*Primary Examiner* — Kent L Bell

(57) ABSTRACT

A new rose plant of the Miniature class which has abundant, apricot pink blend flowers and attractive foliage. This new and distinct variety has shown to be uniform and stable in the resulting generations from asexual propagation.

2 Drawing Sheets

Botanical designation: *Rosa* hybrid.
Variety denomination: 'Poulty024'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulty024', originated as a single seedling from the stated cross.

The new variety may be distinguished from its male pollen parent and female seed parent primarily by the following characteristics. The male pollen parent grows to a height of 30 cm while the new variety grows to a lesser height of 25 cm. The female seed parent has near white flowers, while the new variety has apricot pink blend flower color.

The objective of the hybridization of this rose variety was to create a new and distinct variety with unique qualities, such as:

1. Uniform and abundant apricot pink blend flowers;
2. Vigorous, but compact growth when propagated on its own roots;
3. Exceptional disease resistance.

This combination of qualities is not present in previously available commercial cultivars of this type, known to the inventor, and distinguish 'Poulty024' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulty024' was selected in the spring of 2012 by the inventor as a single plant from the progeny of the aforementioned hybridization.

Asexual reproduction of 'Poulty024' by rooted cuttings was first done by Mogens N. Olesen in the nursery in Fredensborg, Denmark in July, 2012. This initial and other subsequent asexual propagations conducted in controlled environments have demonstrated that the characteristics of 'Poulty024' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty024'. Specifically illustrated in the drawing is an open flower viewed from above, open flower side view, flower petals detached, sepals detached showing receptacle and reproductive flower parts, mature and juvenile leaves. Plants shown are 2 years of age.

DETAILED DESCRIPTION OF THE VARIETY

The following is a description of 'Poulty024',as observed in its growth in a field nursery in Marion County, Oreg.

Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpar039', U.S. Plant Pat. No. 19,062 are compared to 'Poulty024' in Chart 1.

CHART 1

| | 'Poulty024' | 'Poulpar039' |
|---|---|---|
| Petal Count | 45 | 40 |
| Flower Diameter | 40 mm | 60 mm |
| General Tonality of Flower Color | Orange Group 29C | Red Group 56C to Red-Purple Group 62D with intonations of Red Group 49A |

FLOWER AND FLOWER BUD

Blooming habit: Continuous.

Flower bud:

*Size*.—Upon opening, 11 mm in length from base of receptacle to end of bud. Bud diameter is 10 mm.

*Bud form*.—Ovoid.

*Sepal inner surface*.—Color: Yellow-Green Group 146D. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—20 mm long, 7 mm wide.

*Receptacle*.—Texture: Smooth. Size: 4 mm in height, 6 mm wide. Color: Yellow-Green Group 144A. Shape: Campanulate.

*Pedicel*.—Surface: Smooth. Length: 20 mm. Diameter: 2 mm on average. Color: Yellow-Green Group 144A. Strength: Average.

Flower bud development: Flower buds are borne in clusters of 1 to 3 flower buds per stem.

Flower bloom:

*Fragrance*.—Moderate.

*Duration*.—The blooms have a duration on the plant of approximately 10 days. Petals fall cleanly away from plant after flowers have fully matured.

*Size*.—Flower diameter is 40 mm when open. Flower depth is 18 mm.

*Flower shape*.—High centered, double, with a high pointed center which is tightly closed.

Petalage: Under normal conditions, flowers have about 45 petals.

General tonality of flower: Open flowers are Orange Group 29C.

Petal color:

*Outer petals*.—Upper surface: Orange Group 27C with intonations of Red Group 38C at the middle zone. Petal spot Yellow Group 12A. Lower surface: Outer zone is White Group 155A, middle zone is Red Group 39B, with Yellow Group 4A petal spot at the base.

*Inner petals*.—Upper surface: Orange Group 29B with intonations of Orange Group 27C at apex. Petal spot Yellow Group 12A. Lower surface: Outer zone is White Group 155A, middle zone is Red Group 39B, with Yellow Group 4A petal spot at the base.

Petals:

*Petal reflex*.—Slightly reflexed.

*Margin*.—Entire and uniform with point at center of the apex. No undulations.

*Shape*.—Broad and elliptic. Apex shape: Rounded. Base shape: Acute.

*Size*.—20 mm (l)×20 mm (w).

*Texture*.—Smooth.

*Thickness*.—Average.

Reproductive flower parts:

*Pollen*.—None observed.

*Anthers*.—Size: 1 mm in length. Color: Yellow Group 8C. Quantity: 20 on average.

*Filaments*.—Color: Yellow Group 7A. Length: 2 mm.

*Pistils*.—Length: 4 mm. Quantity: 17 on average.

*Stigmas*.—Color: Greyed-Yellow Group 160B.

*Styles*.—Color: Red Group 39A.

*Location of stigmas*.—Superior in location relative to the length of the filaments and the height of the anthers.

*Hips*.—None Observed.

PLANT

Plant growth: Upright, bushy. Plants are 25 cm in height, and 25 cm wide.

Stems:

*Color of juvenile growth*.—Yellow-Green Group 144A with intonations of Greyed-Red Group 181A.

*Color of mature growth*.—Yellow-Green Group 144A.

*Length*.—Canes are about 10 cm from the base of the plant to the flowering portion.

*Diameter*.—About 5 mm.

*Internodes*.—On mature canes about 26 mm between nodes.

*Surface texture*.—Young wood: Smooth. Older wood: Smooth.

Long prickles: None observed.

Plant foliage:

*Compound leaf*.—60 mm (l)×40 (w).

*Quantity*.—3 to 4 leaves per 10 cm of stem on average.

*Leaf bearing angle to the stem*.—60 degrees.

*Color of juvenile foliage*.—Upper side: Yellow-Green Group 144A with intonations of Greyed-Red Group 180B. Lower side: Yellow-Green Group 144B.

*Color of mature foliage*.—Upper side: Yellow-Green Group 146A. Lower side: Yellow-Green Group 147B.

Plant leaves and leaflets:

*Stipules*.—Size: 15 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 25 mm. Diameter: 2 mm. Upper surface color: Yellow-Green Group 144A with intonations of Greyed-Red Group 180B. Lower surface color: Yellow-Green Group 144A.

*Rachis*.—Length: 25 mm. Diameter: 1.5 mm. Upper surface color: Yellow-Green Group 144A with intonations of Greyed-Red Group 180B. Lower surface color: Yellow-Green Group 144A.

*Leaflet*.—Quantity: Normally 5 leaflets. Margins: Serrated. Size: Terminal leaflets are about 25 mm long, 16 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulty024', substantially as illustrated and described herein, due to its abundant apricot pink blend flowers, disease resistance, and extended period of bloom.

* * * * *

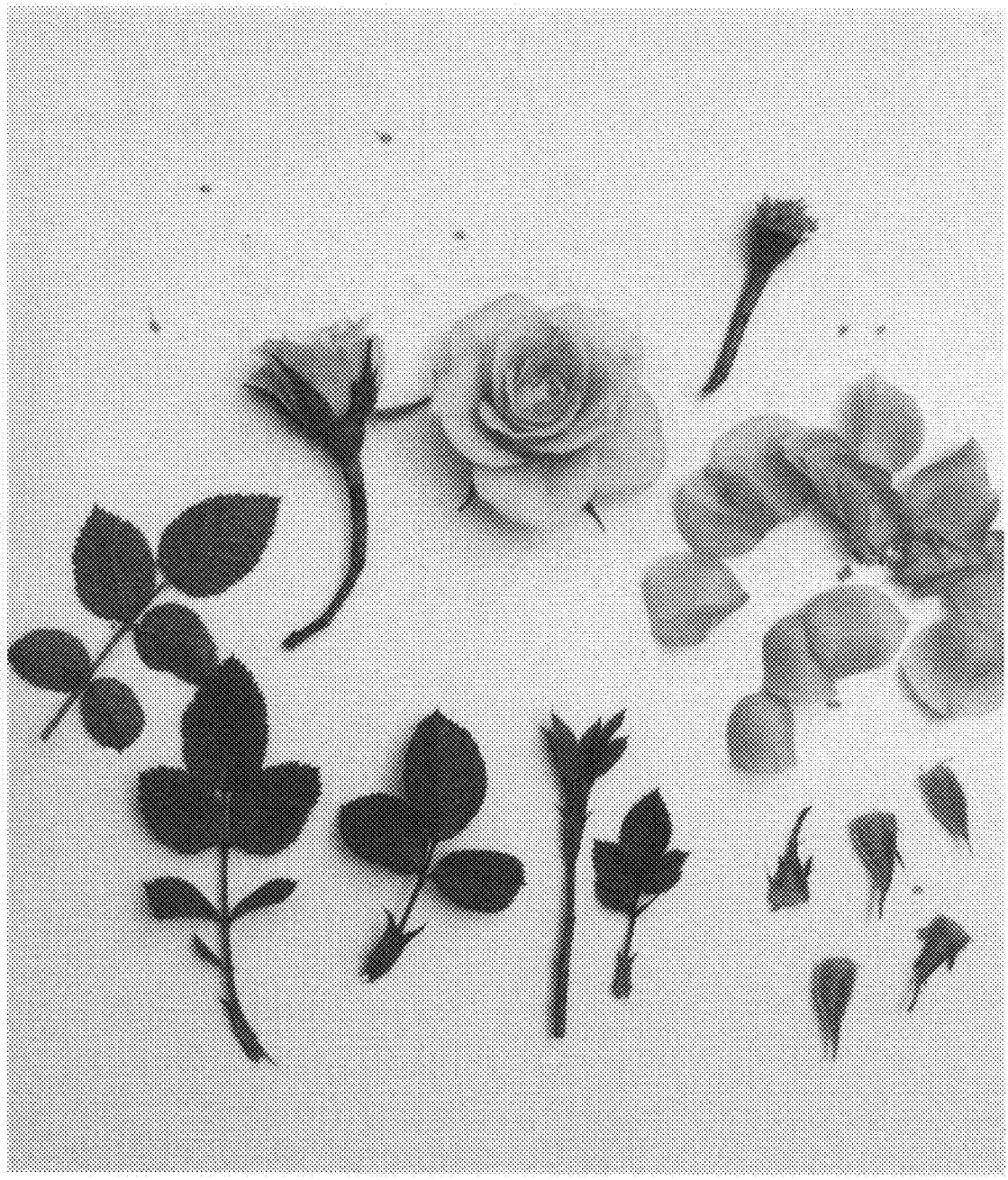

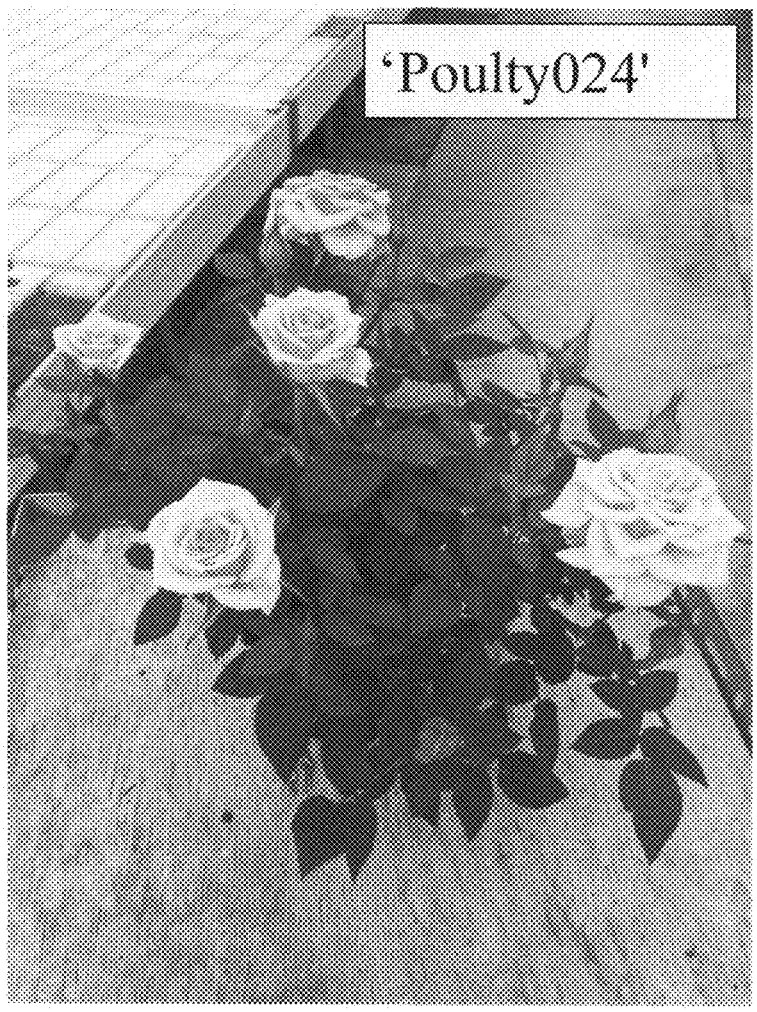
'Poulty024'